United States Patent [19]

McEwen

[11] Patent Number: 5,439,477
[45] Date of Patent: Aug. 8, 1995

[54] TOURNIQUET APPARATUS FOR APPLYING MINIMUM EFFECTIVE PRESSURE

[75] Inventor: James A. McEwen, Richmond, Canada

[73] Assignee: Abatis Medical Technologies, Ltd., Limerick, Ireland

[21] Appl. No.: 128,478

[22] Filed: Sep. 28, 1993

Related U.S. Application Data

[62] Division of Ser. No. 471,514, Jan. 29, 1990, Pat. No. 5,254,087.

[51] Int. Cl.$^6$ .............................................. A61B 5/02
[52] U.S. Cl. .................................................. 606/203
[58] Field of Search ....................... 604/30, 31, 65-67; 606/201-203; 128/677, 686, 783, 744, DIG. 12, DIG. 13

[56] References Cited

U.S. PATENT DOCUMENTS

| | | |
|---|---|---|
| 2,943,859 | 7/1960 | Koski et al. . |
| 3,164,152 | 1/1965 | Vere Nicoll . |
| 3,319,623 | 5/1967 | London . |
| 3,454,010 | 7/1969 | Lilligren et al. . |
| 3,587,584 | 6/1971 | Keller . |
| 3,906,937 | 9/1975 | Aronson . |
| 4,168,063 | 9/1979 | Rowland . |
| 4,321,929 | 3/1982 | Lemelson . |
| 4,469,099 | 9/1984 | McEwen . |
| 4,479,494 | 10/1984 | McEwen . |
| 4,533,346 | 8/1985 | Cosgrove, Jr. et al. . |
| 4,605,010 | 8/1986 | McEwen . |
| 4,635,635 | 1/1987 | Robinette-Lehman . |
| 4,667,672 | 5/1987 | Romanowski . |
| 4,716,906 | 1/1988 | Ruff . |
| 4,718,891 | 1/1988 | Lipps . |
| 4,770,175 | 9/1988 | McEwen . |
| 4,771,790 | 9/1988 | Yamasawa et al. . |

(List continued on next page.)

FOREIGN PATENT DOCUMENTS 2253789 9/1992 United Kingdom .
655385 4/1979 U.S.S.R. .

OTHER PUBLICATIONS

C. M. Holmes, "Intravenous Regional Neural Blockade," in Neural Blockade, M. J. Cousins & P. O. Bridenbaugh, Eds., pp. 443-459, J. B. Lippincott & Co., 1988.

ECRI, "Pneumatic Tourniquets Used for Intravenous Regional Anesthesia," Health Devices, Dec. 1982, pp. 48-49.

S. C. Grice et al., "Intravenous Regional Anesthesia: Prevention of Leakage . . . ", Anesthesiology, vol. 65, pp. 316-320, 1986.

J. A. H. Davies et al., "Intravenous Regional Analgesia: Danger of the Congested Arm and the Value of Occlusion Pressure," Anaesthesia, 1983, vol. 39, pp. 416-421.

E. M. Brown et al., "Intravenous Regional Anesthesia

(List continued on next page.)

Primary Examiner—Stephen C. Pellegrino
Assistant Examiner—Nancy Mulcare
Attorney, Agent, or Firm—Klarquist Sparkman Campbell Leigh & Whinston

[57] ABSTRACT

Tourniquet apparatus for use in intravenous regional anesthesia and limb surgery includes a pressurizing cuff for substantially encircling a limb and applying a varying pressure to an underlying vein in response to variations in a pressure control signal, applied venous pressure sensing means for producing an applied venous pressure signal representative of a pressure applied by the cuff to the underlying vein, venous pressure estimation means for producing a venous fluid pressure signal representative of the pressure of fluid in the vein distal to the cuff, and pressure control means responsive to the venous fluid pressure signal and applied venous pressure signal for generating a pressure control signal to maintain a predetermined relationship between the applied venous pressure signal and the venous fluid pressure signal. The apparatus automatically controls the introduction, retention and release of anesthetic fluid in the limb.

5 Claims, 3 Drawing Sheets

U.S. PATENT DOCUMENTS

| | | |
|---|---|---|
| 4,781,189 | 11/1988 | Vijil-Rosales . |
| 4,869,265 | 9/1989 | McEwen . |
| 4,883,462 | 11/1989 | Williamson . |
| 4,979,953 | 12/1990 | Spence . |
| 5,048,036 | 9/1991 | McEwen . |
| 5,048,536 | 9/1991 | McEwen . |
| 5,103,833 | 4/1992 | Apple . |
| 5,135,473 | 8/1992 | Epler et al. . |
| 5,179,941 | 1/1993 | Siemssen et al. . |
| 5,254,087 | 10/1993 | McEwen .............................. 604/66 |

OTHER PUBLICATIONS (Bier Block): Review of 20 Years' Experience," Can. J. Anaesthesia, 1989, vol. 36, pp. 307–310.

J. Haasio, "Intravenous Regional Anesthesia of the Arm: Effect of the Technique of Exsanguination . . . ," Anaesthesia, vol. 44, pp. 19–21, 1989.

C. Sorbie and P. Chacha, "Regional Anaesthesia by the Intravenous Route," Brit. Med. J., 1965, 1, 957–960.

K. M. El–Hassan et al., "Venous Pressure and Arm Volume Changes During Simulated Bier's Block," Anesthesia, 1984, 39:229–235.

B. A. Finegan & M. D. Bukht, "Venous Pressures in the Isolated Upper Limb . . . ," Can. Anaesthesia Soc. J., 1984, 31:364–7.

R. Sukhani et al., "Lidocaine Disposition . . . With Different Tourniquet Deflation Technics," Anesth. Analg. 1989, 68:633–7.

W. L. Lehman et al., "Intravenous Lidocaine for Anesthesia in the Lower Extremity," J.B.J.S. 66–A, 1984, pp. 1056–1060.

J. H. Davies & A. J. Walford, "Intravenous Regional Anesthesia for Foot Surgery," Aeta. An. Scand., 1986, 30:145–147.

L. N. Nusbaum, "IVRA for Surgery on the Foot and Ankle," Anesthesiology, 64:91–92, 1986.

G. S. Duncan, "The Use of IVRA in Podiatric Surgery," J. Foot Surg., vol. 25, 1986, pp. 411–415.

J. Duggan et al., "Venous Pressures in IVRA," Reg. Anes., 9:70–72, 1984.

T. A. Noel, "Prevention of Leak of Local Anesthesia From Under a Pneumatic Tourniquet," Anesthes., 66:449–450, 1987.

H. Finlay, "A Modification of Bier's Intravenous Analgesia," Anesthesia, 1977, 32:357–358.

TOURNIQUET APPARATUS FOR APPLYING MINIMUM EFFECTIVE PRESSURE

This is a divisional application of U.S. patent application Ser. No. 07/471,514, filed Jan. 29, 1990, now U.S. Pat. No. 5,254,087.

FIELD OF THE INVENTION

This invention pertains to automated tourniquet apparatus for use in intravenous regional anesthesia of a limb for surgery. In particular, the invention pertains to apparatus having means for automatically controlling the introduction, retention and release of anesthetic fluid in a portion of the limb distal to a pressurizing cuff.

BACKGROUND OF THE INVENTION

This invention pertains to apparatus for automating the administration and management of intravenous regional anesthesia (IVRA) for both upper and lower limbs. IVRA is an alternative to general anesthesia for limb surgery. IVRA has proven to be a simple and useful technique for satisfactorily anesthetizing the upper limb and is potentially well suited for greatly expanded utilization in surgery of lower limbs and in outpatient settings. In these settings, which are rapidly increasing in number worldwide, there is a large and unmet need for a rapid, simple, safe, and reliable technique for establishing limb anesthesia. However, significant practical problems with the technology of IVRA in the prior art, considerable variations in skill involving the manual administration of IVRA, and lingering concerns over the potential toxicity of certain IVRA agents, particularly for lower limbs, have greatly limited the acceptance of this promising technique.

IVRA is an anesthetic technique which requires the use of surgical pneumatic tourniquet. Surgical pneumatic tourniquet systems are frequently used on the upper and lower limbs to help maintain a bloodless operative field by regulating the maximum pressure applied to the limb by an encircling cuff at a pressure sufficient to stop arterial blood flow past the cuff for the duration of a surgical procedure. During operations performed under IVRA, the pneumatic tourniquet serves an additional role of preventing local anesthetic agent introduced into the veins in the limb distal to the cuff from flowing proximally past the cuff and out of the limb into the circulatory system. An insufficient pressure in the tourniquet cuff soon after introduction of the local anesthetic agent into the limb may result in the anesthetic agent entering the circulatory system in a high concentration, which can cause serious adverse reactions such as cardiovascular collapse, respiratory depression, epileptic seizures or even death.

IVRA is typically administered as follows. Blood is first exsanguinated from the limb, often by wrapping the limb with an elastic bandage, beginning distally and wrapping tightly towards the heart; after exsanguination, a tourniquet cuff is applied proximal to the operative site and inflated to a predetermined cuff pressure. The elastic bandage is removed and an anesthetic agent such as lidocaine mixed with sterile saline is introduced into a vein in the limb through an intravenous cannula. The anesthetic fluid mixture remains in the veins in the limb as long as the tourniquet is inflated to a sufficient pressure. Premature release of the agent shortly after introduction, as well as leakage of the agent under the cuff during introduction or during surgery, are serious and recognized hazards associated with prior art devices used for IVRA.

Administration of IVRA may involve the use of a single-bladder or a dual-bladder tourniquet cuff. If a dual-bladder cuff has been chosen and applied to the limb of a patient, typically the proximal bladder of the cuff is first inflated, after limb exsanguination, to a pressure intended to prevent blood flow past the cuff both proximally and into the exsanguinated limb. The anesthetic fluid mixture is then introduced into a vein in the limb as described previously. After a period of time sufficient for the anesthetic fluid mixture to induce analgesia in the limb below the proximal bladder of the cuff, the distal bladder is inflated to a pressure intended to prevent the flow of fluid past the cuff both proximally and distally. The distal bladder of the cuff is thus inflated over anesthetized tissue, thereby resulting in greater comfort for the patient for a greater period of time, thus potentially extending both the duration of surgical procedures which can be performed under IVRA and the number of patients for whom IVRA will be tolerable.

Surgical tourniquet systems of the prior art typically include an inflatable cuff for applying to a limb and an automatic pressure regulator for regulating the inflation pressure in the cuff near a reference level selected by an operator or determined automatically. Some tourniquet systems in the prior art have been associated with a number of reported hazards and problems which are not specific to IVRA, such as unnecessarily high pressures applied by the cuff leading to nerve injury and tissue damage beneath the tourniquet cuff, and unexpectedly low pressures applied by the cuff leading to sudden blood flow into the surgical site, complication of surgery, passive congestion of the limb, and hemorrhagic nerve infiltration. Additionally, the cuffs of prior art systems have design limitations which make the cuffs difficult to apply consistently to limbs of different shapes and sizes. These design limitations of many prior art inflatable cuffs and tourniquet systems lead to clinical situations in which the maximum pressure actually applied by a prior art cuff to a limb is significantly different than the pressure in the inflatable bladder of the cuff and thus pressure indicated by the tourniquet pressure display.

There are also specific hazards associated with the use of prior art tourniquet systems for IVRA because the pressure of liquid anesthetic agents introduced into limb veins has generally not been monitored in the prior art, which has led to excessive pressures in the veins distal to the tourniquet cuff, thus causing anesthetic agent to flow past the cuff and into the general circulation. This can lead to an ineffective regional anesthesia in general, and even to cardiac arrest and death in reported cases.

A serious problem associated with the use of prior art tourniquet systems in relation to the delivery of anesthetic agents for IVRA is that in the prior art the maximum pressure applied by the tourniquet cuff to the limb is determined and adjusted independently of, and without knowledge of, the delivery pressure of the anesthetic agent. Moreover, the anesthetic agent is delivered in the prior art manually at a maximum pressure that is highly variable and dependent on the variations in operator technique. Most significantly, in the prior art, the pressure of liquid in the veins distal to the cuff is not a function of the maximum pressure applied by the tourniquet cuff. Consequently, it cannot be assured that the applied pressure is sufficiently greater than the venous pressure distal to the cuff so that no anesthetic agent will flow unexpectedly past the cuff and into the general circulation.

Another problem associated with prior art tourniquet systems is that no provision exists for automatically adjusting the pressure applied by the cuff such that bleeding arterial vessels can be observed in the surgical wound prior to completion of surgery, while the anesthetic fluid mixture is simultaneously retained in the veins of the limb distal to the cuff. Bleeding vessels can be observed only if the applied pressure is reduced sufficiently to permit arterial inflow; however, at the same time the applied pressure must be great enough to stop venous outflow and thereby maintain anesthesia. Prior art tourniquet systems do not provide any methods for reliably establishing and maintaining this condition.

For reasons of improved patient safety, there is a clinical need for wider tourniquet cuffs which appear to stop blood flow distal to such cuffs at lower inflation pressures than narrower cuffs. However, a significant problem with prior art cuffs in general, and with wide cuffs in particular, is that reliable and consistent sealing of the bladders is difficult due to the high forces generated internally because the forces on the sealed seams of bladders are generally proportional to the total internal area of the cuff multiplied by the inflation pressure.

A number of problems are associated specifically with prior art pneumatic cuffs used for IVRA. First, prior art cuffs have generally employed two bladders which can be inflated or deflated independently. Each bladder of an IVRA cuff must be narrower than a conventional tourniquet cuff in order that the IVRA cuff can fit on the patient's limb and not obstruct the desired surgical site. Second, prior art tourniquet cuffs commonly employ a flexible thermoplastic stiffener to constrain the inflation of the bladder and direct cuff inflation inwardly toward the encircled limb. The incorporation of stiffeners into prior art cuffs stabilizes the cuff bladders across the bladder width and thus reduces the tendency of cuffs to roll longitudinally down a limb when the bladders are pressurized. However, certain problems and hazards are associated with the use of prior art stiffeners. First, the incorporation of stiffeners into prior art tourniquet cuffs has tended to cause such cuffs to form a substantially cylindrical shape when applied to a limb, resulting in a poor shape match for limbs that are non-cylindrical in shape in the region underlying the encircling cuff. The use of stiffeners in prior art cuffs has also tended to cause the cuffs to be more difficult to apply by operating room staff in a snug and consistent manner. Also, the incorporation of stiffeners into prior art cuffs has added significantly to the costs of manufacture of such cuffs. Finally, the incorporation of stiffeners into prior art cuffs has created difficulties when the cuffs are cleaned or resterilized because certain resterilization processes apply heat to the cuffs, distorting the shape of stiffeners which are commonly formed of flexible thermoplastic material, thus detrimentally affecting the subsequent ability of the distorted cuff to conform smoothly to the encircled limb.

The present invention overcomes many of the hazards and problems associated with technology described in the prior art and significantly reduces variations in the quality and safety of IVRA associated with variable knowledge, skill and experience of operators. Thus the present invention facilitates the increased use of IVRA for anesthesia of both upper and lower limbs.

An object of the present invention is to provide tourniquet apparatus for intravenous regional anesthesia which automatically relates the maximum pressure applied to a limb by the tourniquet cuff to the maximum pressure of fluid in the veins in a portion of the limb distal to the cuff, so that the flow of fluid past the cuff proximally and into the circulatory system can be automatically regulated and stopped in a safe and reliable manner, as desired by an anesthetist or surgeon.

Another object of the present invention is to provide tourniquet apparatus having automatic means for estimation of the lowest pressure which can be applied by the cuff of the tourniquet apparatus to a limb in order to stop blood flow distal to the cuff, where the cuff has design and physical characteristics which are substantially different than those of a conventional blood pressure cuff, where the cuff is applied with an undetermined degree of snugness at any location along the limb between its proximal and distal end, and where there may be a substantial mismatch between the shape of the encircled limb and the shape of the encircling cuff.

A related object is to provide tourniquet apparatus having wider and safer cuffs for reducing the probability that blood will unexpectedly flow past the cuff distally, for reducing the probability that anesthetic fluid mixture will unexpectedly flow past the cuff proximally, for reducing the probability that clinical staff will make errors in applying the cuff to the correct location anatomically, and for increasing the tolerance of the patient to the cuff when pressurized so that more patients can take advantage of intravenous regional anesthesia.

Another object of the present invention is to provide means for more consistent and safer exsanguination of a portion of the limb distal to the tourniquet cuff prior to introduction of anesthetic agent into a vein in that limb portion, by automatically regulating the pressure in a pneumatic exsanguinating cuff distal to the tourniquet cuff for a period of time, and by automatically and sequentially inflating the tourniquet cuff proximal to the exsanguinating cuff when sufficient blood has been exsanguinated from the surrounded portion.

The applicant is aware of the following United States Patents which are more or less relevant to the subject matter of the applicant's invention.

| | | | |
|---|---|---|---|
| 4,469,099 | 9/1984 | McEwen | 128/327 |
| 4,479,494 | 10/1984 | McEwen | 128/327 |
| 4,605,010 | 9/1986 | McEwen | 128/686 |
| 4,770,175 | 9/1988 | McEwen | 128/327 |
| 4,869,265 | 9/1989 | McEwen | 128/774 |
| 4,321,929 | 3/1982 | Lemelson | 128/630 |
| 4,635,635 | 1/1987 | Robinette-Lehman | 128/327 |
| 4,781,189 | 11/1988 | Vijil-Rosales | 128/327 |
| 4,168,063 | 9/1979 | Rowland | 273/54B |
| 3,164,152 | 1/1965 | Vere Nicoll | 128/87 |
| 4,667,672 | 5/1987 | Romanowski | 128/327 |

The applicant is also aware of the following United States patent application which is more or less relevant to the subject matter of the applicant's invention. U.S. application Ser. No. 388,669; Title: Tourniquet for Regulating Applied Pressures; Art Unit: 335; Inventor: McEwen.

SUMMARY OF THE INVENTION

The invention is directed toward tourniquet apparatus for controlling the release of anesthetic fluid contained in a limb vein distal to a pressurized cuff, comprising: a pressurizing cuff for substantially encircling a limb and applying a varying pressure to an underlying vein in response to variations in a pressure control signal; applied venous pressure sensing means for producing an applied venous pressure signal representative of a pressure applied by the cuff to the underlying vein; venous fluid pressure estimation means for producing a venous fluid pressure signal representative of the pressure of fluid in the vein distal to the cuff; and pressure control means responsive to the venous fluid pressure signal and applied venous pressure signal for generating a pressure control signal to maintain a predetermined relationship between the applied venous pressure signal and the venous fluid pressure signal. The venous fluid pressure estimation means may be a signal representative of a predetermined constant reference pressure. Interval selection means may be included for determining a first time interval and a second time interval wherein the pressure control means generates a pressure control signal so that during the first time interval the pressure applied by the cuff to the underlying vein is greater than the minimum pressure which stops the flow of fluid in the vein past the cuff proximally, and during the second time interval the pressure applied by the cuff to the vein is less than the minimum pressure which stops the flow of fluid in the vein past the cuff proximally.

The invention is also directed to improved cuff apparatus for use in intravenous regional anesthesia comprising an occlusive band for applying pressure to a limb, and locating means on the band for locating the band on the limb at a predetermined distance from an anatomical reference site.

The invention is further directed to apparatus for estimating the minimum pressure which must be applied by a cuff to a limb in order to stop blood flow past the cuff, comprising: a pressurizing cuff responsive to cuff pressure control means for substantially encircling and applying pressure to a limb; distal flow sensing means for sensing the flow of blood past the pressurizing cuff; cuff pressure control means for controlling the pressure applied by the pressurizing cuff to the limb near a reference pressure; and flow detection means responsive to the distal flow sensing means for varying the reference pressure to estimate the lowest reference pressure at which no blood flow can be sensed past the pressurizing cuff. The pressurizing cuff may be a tourniquet cuff having design and construction characteristics substantially different than those of a cuff required for accurate estimation of blood pressure at the selected location by a noninvasive technique. Advantageously, occlusion pressure estimation means responsive to the lowest reference pressure at which no blood flow can be sensed past the pressurizing cuff may be included for producing an estimate of the lowest constant reference pressure at which no blood will flow past the pressurizing cuff over a time period that is suitably long for the performance of a surgical procedure.

The invention is also directed to automatic exsanguinating tourniquet apparatus to facilitate intravenous regional anesthesia comprising: occlusive cuff means for encircling a limb and applying a pressure to the encircled limb portion; exsanguinating cuff means for surrounding and applying a pressure to a portion of the limb distal to the occlusive cuff means; first reference pressure means for producing a first pressure signal representative of a pressure to be applied by the exsanguinating cuff means to displace blood from the portion of the limb surrounded by the exsanguinating cuff means; second reference pressure means for producing a second pressure signal representative of a pressure to be applied by the occlusive cuff means to occlude blood flow distal to the occlusive cuff means; and automatic pressure regulating means for regulating pressure applied by the exsanguinating means near a pressure indicated by the first pressure signal for a first period of time, and for regulating a pressure applied by the occlusive means near a pressure indicated by the second pressure signal for a second period of time suitably long for the performance of a surgical procedure.

DESCRIPTION OF THE PREFERRED EMBODIMENT

The embodiment illustrated is not intended to be exhaustive or to limit the invention to the precise form disclosed. It is chosen and described in order to explain the principles of the invention and its application and practical use, and thereby enable others skilled in the art to utilize the invention.

Figure 1:
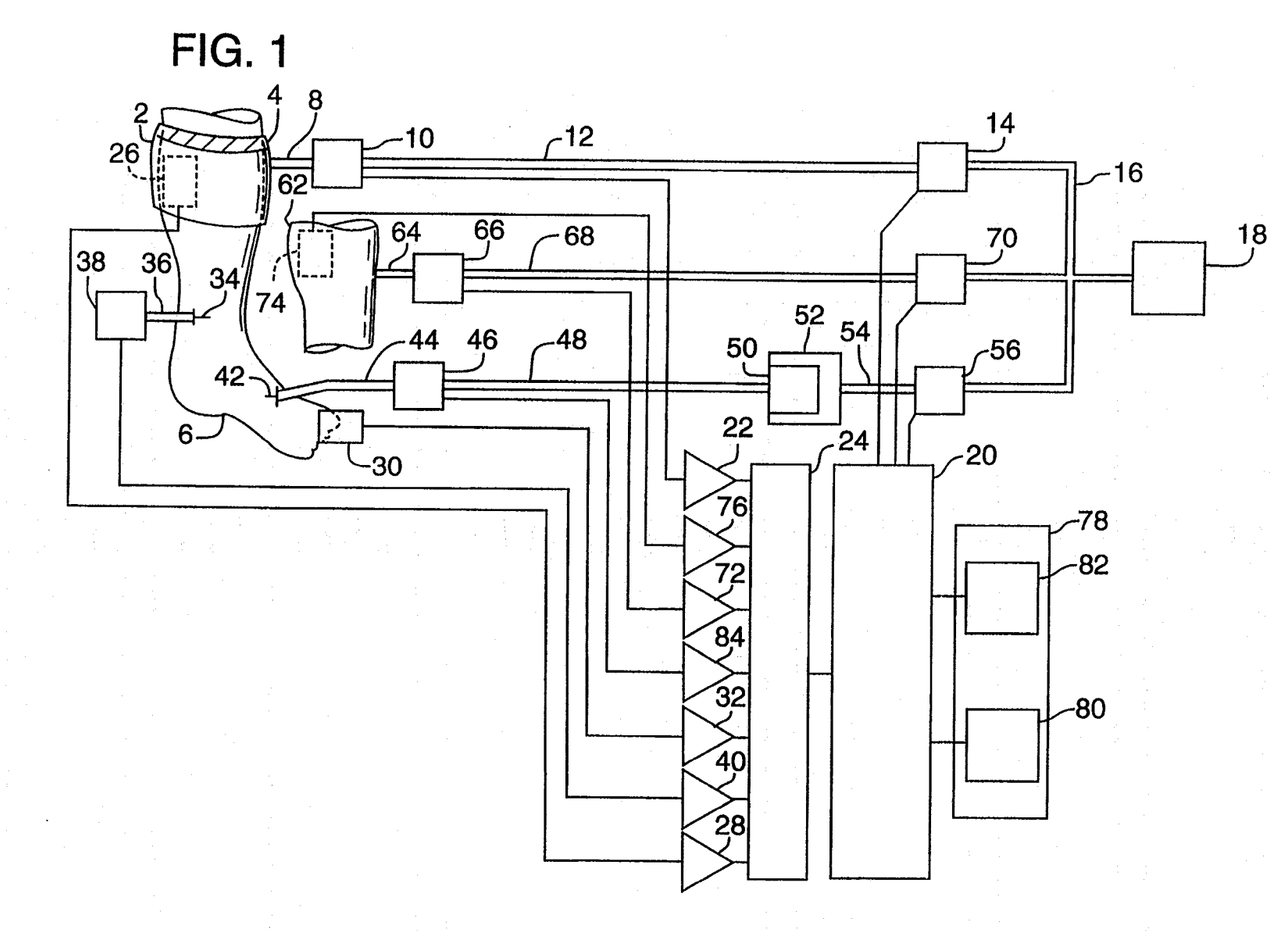
FIG. 1 is a block diagram of the preferred embodiment.

Referring to FIG. 1, an inflatable tourniquet cuff 2, which has locating strip 4 for positioning cuff 2 relative to an anatomical landmark, is applied to limb 6. Cuff 2 is connected by tubing 8 to pressure transducer 10 (Spectramed 072911-000-583, Spectramed Inc., Oxnard, Calif.), and then by tubing 12 to valves 14 (EVO-3-12 V, Clippard Instrument Laboratory, Cincinnati, Ohio). Valves 14 allow tubing 12 to be connected to tubing 16 and pressure source 18 which provides a source of gas at a regulated pressure between zero and 500 mmHg. This arrangement provides a means of inflating cuff 2 to apply a distribution of pressures varying from zero to some maximum level to the tissues and blood vessels of limb 6 beneath cuff 2, with the specific pressure distribution dependent upon cuff design and application technique. Valves 14 are controlled by an applied pressure control signal generated by microcomputer 20. Pressure transducer 10 generates an inflation pressure signal which indicates the pressure of gas in cuff 2 and which is processed by signal conditioner 22, digitized by analog to digital converter (ADC) 24, and communicated to microcomputer 20. Limb pressure sensor 26, such as the biomedical pressure transducer described by McEwen in U.S. Pat. No. 4,869,265, is placed underneath cuff 2 at a location such that the maximum pressure applied by cuff 2 to limb 6 is transduced. Limb pressure sensor 26 generates an applied pressure signal which is indicative of that maximum pressure. The applied pressure signal is processed by signal conditioner 28, digitized by ADC 24, and communicated to microcomputer 20. Photoplethysmographic flow sensor 30 is placed on a portion of limb 6 distal to cuff 2 in order to sense blood flow in limb 6. Sensor 30 generates a blood flow signal which is processed by signal conditioner 32, digitized by ADC 24, and communicated to microcomputer 20. Cannula 34 is inserted in a vein in limb 6 distal to cuff 2 and is connected by tubing 36 to pressure transducer 38 to allow estimation of the venous fluid pressure; pressure transducer 38 generates a venous fluid pressure signal which is processed by signal conditioner 40, digitized by ADC 24, and communicated to microcomputer 20. Cannula 42 is inserted in a vein in limb 6 distal to cuff 2 and is connected by tubing 44 to pressure transducer 46; pressure transducer 46 is connected by tubing 48 to anesthetic container 50 which holds a fluid anesthetic such as lidocaine mixed with a sterile saline solution; anesthetic container 50 is typically a sterile saline bag in which the fluid anesthetic has been previously introduced with a syringe. The mixture of fluid anesthetic and sterile saline is delivered by delivery module 52; delivery module 52 applies a pressure to anesthetic container 50 and thereby forces the mixture from anesthetic container 50 into the vein through cannula 42. Delivery module 52 is connected by tubing 54 and valves 56 to pressure source 18. Valves 56, which control the delivery pressure of the anesthetic fluid mixture, are responsive to the delivery pressure control signal. Pressure transducer 46 generates a delivery pressure signal representative of the anesthetic fluid mixture pressure which is processed by signal conditioner 84, digitized by ADC 24, and communicated to microcomputer 20.

Figures 2, 4, 5, 6, 7:
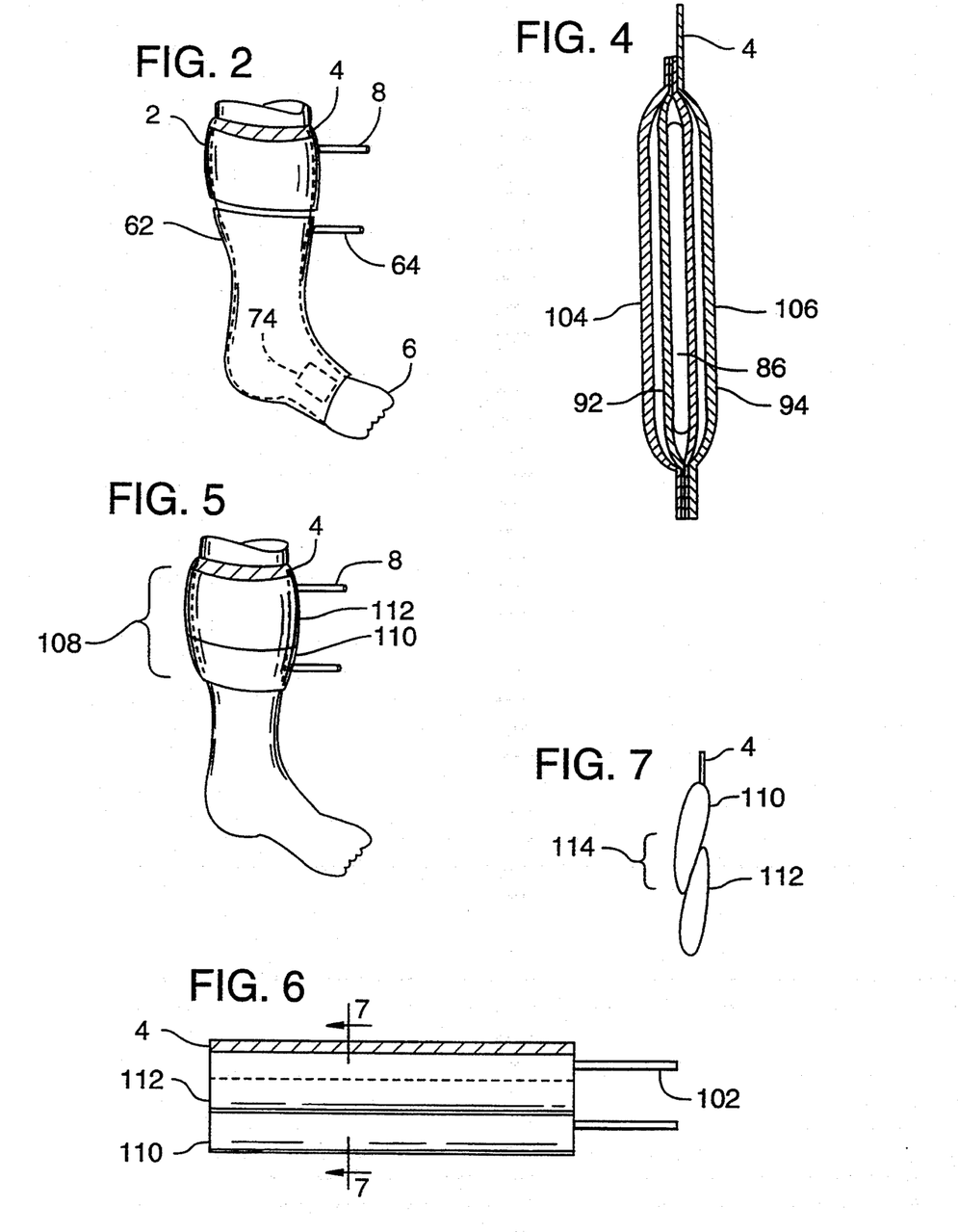
FIG. 2 is a pictorial representation of the application to a limb of the cuffs of the preferred embodiment in FIG. 1.
FIG. 4 is a sectional view taken along line 4—4 of FIG. 3.
FIG. 5 is a pictorial representation of the application to a limb of the dual-bladder cuff of the preferred embodiment.
FIG. 6 is a plan view of the dual-bladder cuff shown in FIG. 5.
FIG. 7 is a sectional view taken along line 7—7 of FIG. 6.

FIG. 2 shows exsanguinating cuff 62 applied to limb 6. Referring to FIG. 1, exsanguinating cuff 62, such as the Jobst-Jet Air Splint (Jobst Institute Inc., Toledo, Ohio) of a size appropriate for the portion of limb 6 to be exsanguinated, is connected through tubing 64 to pressure transducer 66; pressure transducer 66 is connected through tubing 68 and valves 70 to pressure source 18. This arrangement provides exsanguinating cuff 62 with a means of inflation. Valves 70 are operated by an exsanguinating control signal from microcomputer 20 in order to vary the pressure in exsanguinating cuff 62. This produces a variation in the distribution of pressures applied by exsanguinating cuff 62 to limb 6. Pressure transducer 66 generates an exsanguinating pressure signal which is processed by signal conditioner 72, digitized by ADC 24, and communicated to microcomputer 20. Doppler blood flow sensor 74 positioned under exsanguinating cuff 62 over an artery in limb 6 generates a residual blood signal which is processed by signal conditioner 76, digitized by ADC 24, and communicated to microcomputer 20.

The user communicates with the system by means of user panel 78. Switches 80 on user panel 78 are used to input information and commands from the user to microcomputer 20, and microcomputer 20 reports pressures, system status, and alarms to the user by audio/visual display 82.

In operation, the user instructs microcomputer 20 by means of user panel 78 to automatically estimate the lowest reference pressure at which no blood flow can be sensed past cuff 2 by photoplethysmographic blood flow sensor 30. This is accomplished by varying the reference pressure which causes the maximum pressure applied by cuff 2 to vary accordingly, and by monitoring the resulting variations in blood flow distal to cuff 2 as follows. Microcomputer 20 produces an applied pressure control signal which activates valves 14 to inflate cuff 2, thereby causing the maximum pressure applied to limb 6 by cuff 2 to increase as indicated by the applied pressure signal produced by sensor 26. While the reference pressure is being increased, microcomputer 20 detects the lowest applied pressure at which the flow signal falls below a predetermined threshold near zero. This value of the applied pressure is an estimate of lowest reference pressure which stops blood flow past cuff 2. Microcomputer 20 then acts to increase the applied pressure to 20 mmHg above this lowest reference pressure, after which an applied pressure control signal is generated to deflate cuff 2, thereby decreasing the applied pressure. While cuff 2 is being deflated, microcomputer 20 monitors the blood flow signal from sensor 30 and detects the applied pressure at which the flow signal exceeds the predetermined threshold. This value of the applied pressure is an estimate of the highest reference pressure at which blood flow past cuff 2 can be sensed. Microcomputer 20 then calculates the mean of the highest reference pressure and lowest reference pressure thus obtained and adds 75 mmHg to this mean value, thereby producing an estimate of the lowest constant reference pressure at which no blood will flow past cuff 2 over a time period which is suitably long for the performance of a surgical procedure. Once the lowest constant reference pressure has been estimated, blood flow sensor 30 is removed if clinically desired. For unusual clinical situations in which a blood flow signal cannot be detected by microcomputer 20, provision is made for an estimate of the lowest constant reference pressure to be entered manually by the user through user panel 78.

Following the estimation of the lowest constant reference pressure, the user instructs microcomputer 20 with switches 80 on user panel 78 to exsanguinate the portion of limb 6 surrounded by exsanguinating cuff 62. This is accomplished as follows. Microcomputer 20 generates an exsanguinating control signal which activates valves 70 and thus causes exsanguinating cuff 62 to inflate to a predetermined inflation pressure of approximately 100 mmHg. The pressure applied to limb 6 by exsanguinating cuff 62 is regulated at a constant level by microcomputer 20 using pressure transducer 66 and valves 70. Microcomputer 20 monitors the residual blood signal from Doppler blood flow sensor 74 to determine the period of time that the constant pressure is applied in order to displace a significant volume of blood from the portion of limb 6 surrounded by exsanguinating cuff 62. As exsanguinating cuff 62 inflates, the amplitude of the pulsatile signal detected by Doppler blood flow sensor 74 decreases, thereby providing an indication that arterial inflow is being reduced. After the amplitude of the residual blood signal has fallen below a threshold near zero, the pressure is maintained at the constant level for two minutes, after which the portion of limb 6 surrounded by exsanguinating cuff 62 is considered to be adequately exsanguinated. For unusual situations in which a residual blood signal cannot be obtained by microcomputer 20 from sensor 74, provision is made for the user to define the period of time exsanguinating cuff 62 is to remain inflated. Microcomputer 20 then generates an applied pressure control signal to inflate cuff 2 to the lowest constant reference pressure previously estimated as described above. This stops blood flow past cuff 2 in the exsanguinated portion of limb 6 distal to cuff 2. Thereafter, microcomputer 20 continues to automatically regulate the maximum pressure applied to limb 6 by cuff 2 near the lowest constant reference pressure to stop blood flow past cuff 2 for a period of time suitably long for the performance of a surgical procedure.

After exsanguination, cannula 34 is inserted into a vein in limb 6 distal to cuff 2, and cannula 42 is inserted into a vein in limb 6 appropriate for introduction of the anesthetic fluid mixture. Microcomputer 20 is then instructed by the user through user panel 78 to deliver the anesthetic fluid mixture at a maximum pressure such that the anesthetic fluid mixture does not flow proximally past cuff 2. Microcomputer 20 analyses the applied pressure signal from limb pressure sensor 26 and the delivery pressure signal from transducer 46 in order to generate a delivery control signal such that the ratio of the delivery pressure signal to the applied pressure signal is less than 0.75. Microcomputer 20 does not allow the delivery pressure to exceed a maximum level of 100 mmHg for safety reasons. In an unusual clinical situation when the delivery pressure cannot be controlled, such as when the user may have to pressurize anesthetic container 50 manually, provision is included for stopping the flow of the anesthetic fluid mixture past cuff 2 proximally by increasing the pressure applied to the limb. This is done by having microcomputer 20 monitor the delivery pressure signal by means of transducer 46 and generate an applied pressure control signal such that the ratio of the delivery pressure signal to the applied pressure signal is less than 0.75.

Once the anesthetic fluid mixture has been delivered to a vein in limb 6, it must be retained in the portion of limb 6 distal to cuff 2 during most of the surgical procedure and released near the end of the surgical procedure. The flow of anesthetic fluid mixture past cuff 2 is controlled according to the following algorithm. Microcomputer 20 monitors the applied pressure signal from sensor 26 and the venous fluid pressure signal from transducer 38. Microcomputer 20 then generates an applied pressure control signal such that the maximum pressure applied by cuff 2 is regulated at a pressure at least 50 mmHg above the venous fluid pressure. Because the maximum applied pressure is at least 50 mmHg greater than the venous fluid pressure, the anesthetic fluid mixture is retained within limb 6.

When release of the anesthetic fluid mixture from limb 6 is desired, microcomputer 20 generates an applied pressure control signal such that the maximum pressure applied by cuff 2 is regulated at a level below the venous fluid pressure to allow outflow of the anesthetic fluid mixture. In clinical cases where it is important to identify bleeding arterial vessels in the surgical site prior to completion of surgery without releasing the anesthetic fluid mixture from limb 6, the user can cause microcomputer 20 to generate an applied pressure control signal such that the maximum pressure applied by cuff 2 is regulated at a pressure less than the lowest constant reference pressure previously determined, but above the venous fluid pressure. In this way, arterial blood flows past cuff 2 distally, but venous fluid does not flow past cuff 2 proximally. This provision significantly extends the range of surgical procedures in which intravenous regional anesthesia can be used.

In a condition where it is not possible to use cannula 34 and transducer 38 to estimate venous fluid pressure, provision is included for microcomputer 20 to substitute 20 mmHg for the venous fluid pressure.

Near the end of the surgery, the user instructs microcomputer 20 to release the anesthetic fluid mixture from limb 6 in a controlled manner over a period of time with user panel 78. This is accomplished as follows. First, microcomputer 20 generates an applied pressure control signal so that the maximum pressure applied by cuff 2 is regulated at a pressure which allows venous outflow from limb 6 for a period of 10 s to allow a portion of the anesthetic fluid mixture to be released from the vein of limb 6. Microcomputer 20 then generates an applied pressure control signal so that the maximum pressure applied by cuff 2 is regulated at a higher pressure so that any flow of the anesthetic fluid mixture past cuff 2 is stopped. This higher pressure is regulated for a period of 60 s in order to allow assimilation of the anesthetic fluid mixture and venous blood into the general circulation. The foregoing sequence of increasing and decreasing the maximum pressure applied to limb 6 by cuff 2 is repeated three times, after which cuff 2 is completely depressurized. This procedure allows for complete release of the anesthetic fluid mixture from limb 6 in a safe manner. Provision has been made so that the time interval over which the applied pressure remains at the lower pressure, the time interval over which the applied pressure remains at the higher pressure, and the number of times that the applied pressure is cyclically decreased and then increased can be overridden or changed.

Figure 3:
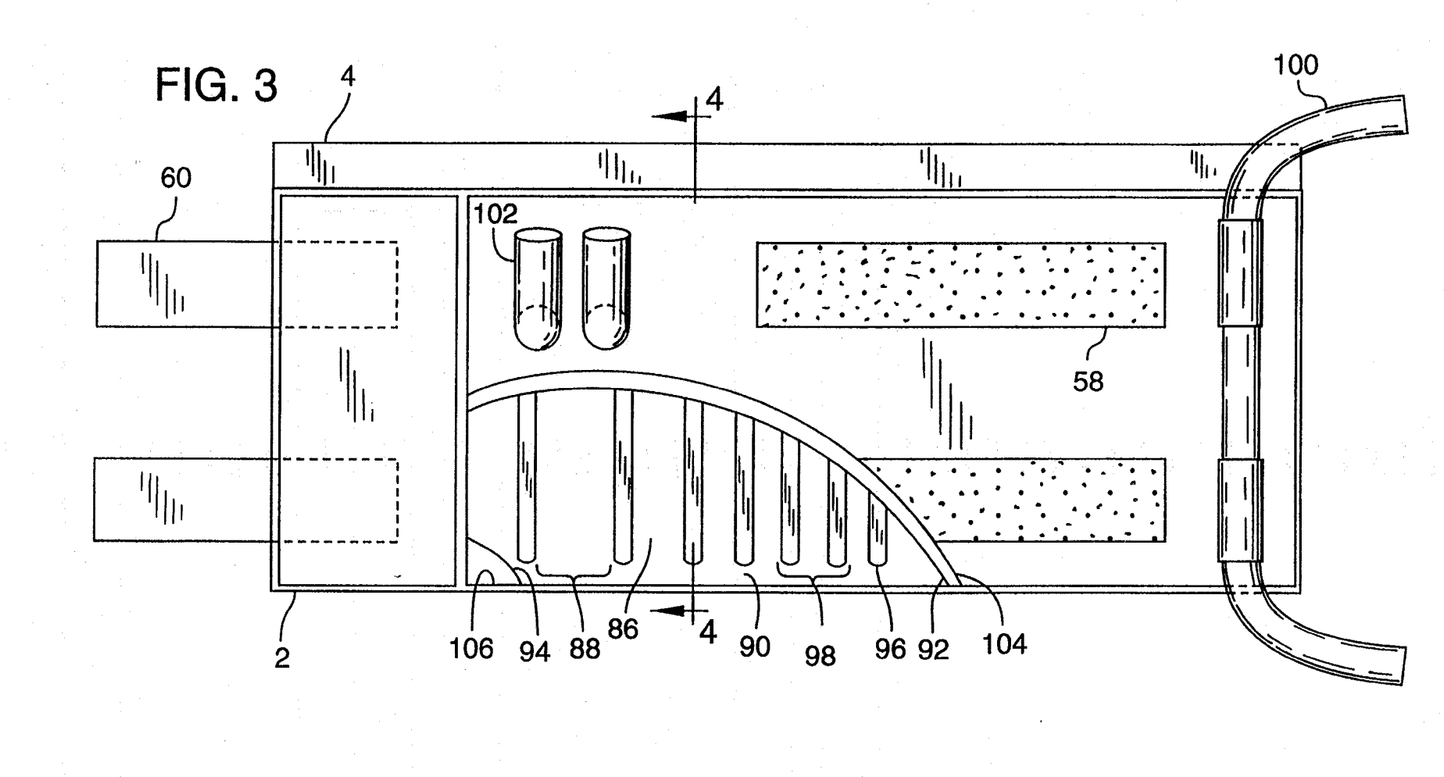
FIG. 3 is a cut-away view of the inflatable tourniquet cuff of the preferred embodiment.

FIG. 3 shows details of inflatable tourniquet cuff 2. Cuff 2 is fabricated as described by Robinette-Lehman in U.S. Pat. No. 4,635,635. In contrast to Robinette-Lehman, as can be seen in FIGS. 3 and 4, cuff 2 has no stiffener, is not arcuate in shape, includes locating strip 4 for positioning cuff 2 on limb 6 at a predetermined distance from an anatomical landmark, is substantially different in width, and is otherwise different as described below.

As can be seen in FIG. 3, tourniquet cuff 2 has an inflatable chamber 86 which includes a plurality of elongated tubular portions 88 which are connected in a generally parallel array, and which are in fluid communication by passageways 90. Tubular portions 88 are formed by joining together at seams 96 two plastic layers 92,94 which form the walls of inflatable chamber 86. Cuffs having chamber widths of 15, 20 and 25 cm, instead of the conventional maximum width of less than 9 cm, were fabricated. Fabrication of these wider cuffs was possible because the plurality of tubular portions 88 in inflatable chamber 86 act to significantly reduce the forces on seams 96, because the forces on seams 96 are generally proportional to the total internal area bounded by seams 96 multiplied by the inflation pressure.

The tubular portions 88, their adjacent seams 96, and passageways 90 are hereinafter referred to as flutes 98. The plurality of elongated tubular portions 88 in inflatable chamber 86 stiffens cuff 2 and allows for a desired distribution of pressure to be applied to limb 6 by choosing appropriate distances between seams 96, since varying these distances results in a change in the pressure distribution underlying cuff 2. Cuff 2 is wrapped about limb 6 and is held in place by female Velcro strips 58 and male Velcro strips 60. Cuff 2 is further held in place by tying together the ends of strap 100 after cuff 2 has been applied to limb 6. Cuff 2 is inflated with gas via ports 102.

FIG. 4 is a sectional view of inflatable tourniquet cuff which shows inflatable chamber 86 and two outer layers 104,106.

For certain surgical procedures of long duration, dual-bladder cuff 108 depicted in FIGS. 5, 6, and 7 is used for increased comfort. In cuff 108, two bladders 110, 112 overlap and are permanently bonded together such that 30 percent of the width of each bladder lies within the overlapping region 114. Bladders 110, 112 are independently and selectably inflatable by appropriate valves and switching. The overlapping of bladders 110,112 around limb 6 in a predefined relationship distributes the pressure applied by each bladder over a greater length along limb 6 than would be possible if narrower bladders which did not overlap occupied the same total width. Distribution of pressures over a greater length along the limb in this manner lowers the maximum pressure which must be applied to prevent fluid flow past cuff 108 thereby resulting in a reduced risk of underlying nerve injury and greater comfort for the patient. Locating strip 4, which is 1.5 inches wide, cannot be inflated. Locating strip 4 permits an unskilled user to accurately and consistently apply cuff 108 at a fixed distance from an anatomical reference site. In lower limb surgery, for example, the top of locating strip 4 is positioned on the head of the fibula so that the top of cuff 108 encircles limb 6 approximately 1.5 inches distal to the head of the fibula. This reduces the likelihood of a compression injury to the peroneal nerve below the head of the fibula following pressurization of cuff 108.

It is to be understood that the invention is not to be limited to the details herein given but may be modified within the scope of the appended claims.

What is claimed is:

1. Tourniquet apparatus for maintaining the lowest constant pressure applied by a pressurizing cuff to a limb to stop blood flow past the cuff for the duration of a surgical procedure, comprising:

a) a pressurizing cuff responsive to cuff pressure control means for substantially encircling and applying pressure to a limb;
   b) distal flow sensing means for sensing the flow of blood past the pressurizing cuff;
   c) cuff pressure control means for controlling the pressure applied by the pressurizing cuff to the limb in response to a cuff pressure control signal;
   d) signal generating means responsive to the distal flow sensing means for generating a variable signal indicative of varying pressure to be applied by the cuff to the limb;
   e) estimation means for producing an estimate of a pressure level to be applied by the cuff to the limb so that the sensed blood flow is below a threshold level near zero;
   f) constant pressure means for producing a constant signal that is greater than the estimate and is indicative of a constant reference pressure to be applied by the cuff to the limb to stop blood flow past the cuff for the duration of a surgical procedure; and
   g) selection means for selecting either the variable signal or the constant signal to be the cuff pressure control signal.

2. Apparatus as defined in claim 1 wherein the estimate produced by the estimation means is indicative of the lowest pressure at which no blood flow can be sensed past the pressurizing cuff.

3. Apparatus as defined in claim 1 wherein the estimate produced by the estimation means is indicative of the highest pressure at which blood flow can be sensed past the cuff.

4. Apparatus as defined in claim 2 wherein the estimation means also produces a second estimate indicative of the highest pressure at which blood flow can be sensed past the pressurizing cuff, and wherein the constant pressure means is responsive to the estimation means for producing a constant signal that is a function of the first-mentioned estimate and the second estimate.

5. Apparatus as defined in claim 1 wherein the estimate produced by the estimation means is indicative of the highest pressure at which blood flow can be sensed past the pressurizing cuff.

* * * * *